(12) United States Patent
Kok et al.

(10) Patent No.: US 10,959,693 B2
(45) Date of Patent: Mar. 30, 2021

(54) DEVICE AND METHOD FOR ALIGNING AN X-RAY GRATING TO AN X-RAY RADIATION SOURCE, AND X-RAY IMAGE ACQUISITION SYSTEM

(71) Applicants: KONINKLIJKE PHILIPS N.V., Eindhoven (NL); NEDERLANDSE ORGANISATIE VOOR TOEGEPAST-NATUURWETEN SCHAPPELIJK ONDERZOEK TNO, The Hague (NL)

(72) Inventors: Christiaan Kok, Eindhoven (NL); Gereon Vogtmeier, Aachen (DE); Thomas Koehler, Eindhoven (NL); Johannes Wilhelmus Maria Jacobs, Boxtel (NL); Sandeep Unnikrishnan, Veldhoven (NL); Dorothee Hermes, Eindhoven (NL); Antonius Maria Bernardus Van Mol, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/500,858

(22) PCT Filed: Dec. 10, 2018

(86) PCT No.: PCT/EP2018/084084
§ 371 (c)(1),
(2) Date: Oct. 4, 2019

(87) PCT Pub. No.: WO2019/115419
PCT Pub. Date: Jun. 20, 2019

(65) Prior Publication Data
US 2020/0297297 A1 Sep. 24, 2020

(30) Foreign Application Priority Data
Dec. 12, 2017 (EP) ................................ 17206588

(51) Int. Cl.
*G01N 23/04* (2018.01)
*A61B 6/00* (2006.01)

(52) U.S. Cl.
CPC ............ *A61B 6/484* (2013.01); *A61B 6/4291* (2013.01)

(58) Field of Classification Search
CPC   A61B 6/484; A61B 6/4291; G21K 2207/005; G21K 1/02; G21K 1/06
See application file for complete search history.

(56) References Cited

U.S. PATENT DOCUMENTS

2005/0117170 A1*   6/2005   Hasegawa ............... G03F 7/706
                                                                356/521
2007/0183562 A1    8/2007   Popescu
(Continued)

FOREIGN PATENT DOCUMENTS

| DE | 10136795 A1 | 2/2003 |
| JP | 2011206161 A | 7/2001 |
| WO | WO2011070493 A1 | 6/2011 |

OTHER PUBLICATIONS

PCT International Search Report, International application No. PCT/EP2018/084084, dated Feb. 14, 2019.

*Primary Examiner* — Kiho Kim
(74) *Attorney, Agent, or Firm* — Larry Liberchuk

(57) ABSTRACT

The present invention relates to a device for aligning an X-ray grating to an X-ray radiation source, the device (10) comprising at least two flat X-ray grating segments (11-19); at least one alignment unit (31-39) for aligning one of the at least two flat X-ray grating segments; wherein the at least two flat X-ray grating segments (11-19) are arranged in juxtaposition and are forming an X-ray grating (20); wherein the at least two flat X-ray grating segments (11-19) each comprise a grating surface (41-49) for X-ray radiation, each grating surface (41-49) comprising a geometrical center;

(Continued)

wherein normals (21-29) to each of the grating surfaces (41-49) define a common plane (73), wherein the normals (21-29) intersect the geometrical center of the grating surface (41-49); wherein at least a first of the at least two flat X-ray grating segments (11-19) is rotatable around an axis (131-139) that is perpendicular to the common plane (73); and wherein the first of the at least two flat X-ray grating segments (11-19) that is rotatable around the axis (131-139) is connected to a first of the at least one alignment unit (31-39). The invention provides a device (10) and a method (100) which provide an improved X-ray grating (20).

14 Claims, 4 Drawing Sheets

(56) References Cited

U.S. PATENT DOCUMENTS

| | | | |
|---|---|---|---|
| 2007/0183579 A1* | 8/2007 | Baumann | A61B 6/4291 378/145 |
| 2011/0235780 A1* | 9/2011 | Tada | G01N 23/041 378/62 |
| 2011/0243300 A1 | 10/2011 | Kaneko | |
| 2012/0307966 A1* | 12/2012 | Roessl | A61B 6/4291 378/16 |
| 2013/0315373 A1* | 11/2013 | Rossl | G21K 1/06 378/62 |
| 2015/0055744 A1* | 2/2015 | Anton | A61B 6/4291 378/36 |
| 2015/0092915 A1* | 4/2015 | Anton | A61B 6/4283 378/36 |
| 2016/0128665 A1* | 5/2016 | Roessl | G01N 23/20075 378/36 |
| 2017/0082559 A1* | 3/2017 | Arboleda | G21K 1/025 |
| 2017/0202528 A1 | 7/2017 | Roessl | |
| 2017/0258423 A1* | 9/2017 | Bartl | A61B 6/4035 |
| 2018/0226167 A1* | 8/2018 | Doki | G02B 5/1838 |
| 2019/0261936 A1* | 8/2019 | Deutinger | A61B 6/4035 |

* cited by examiner

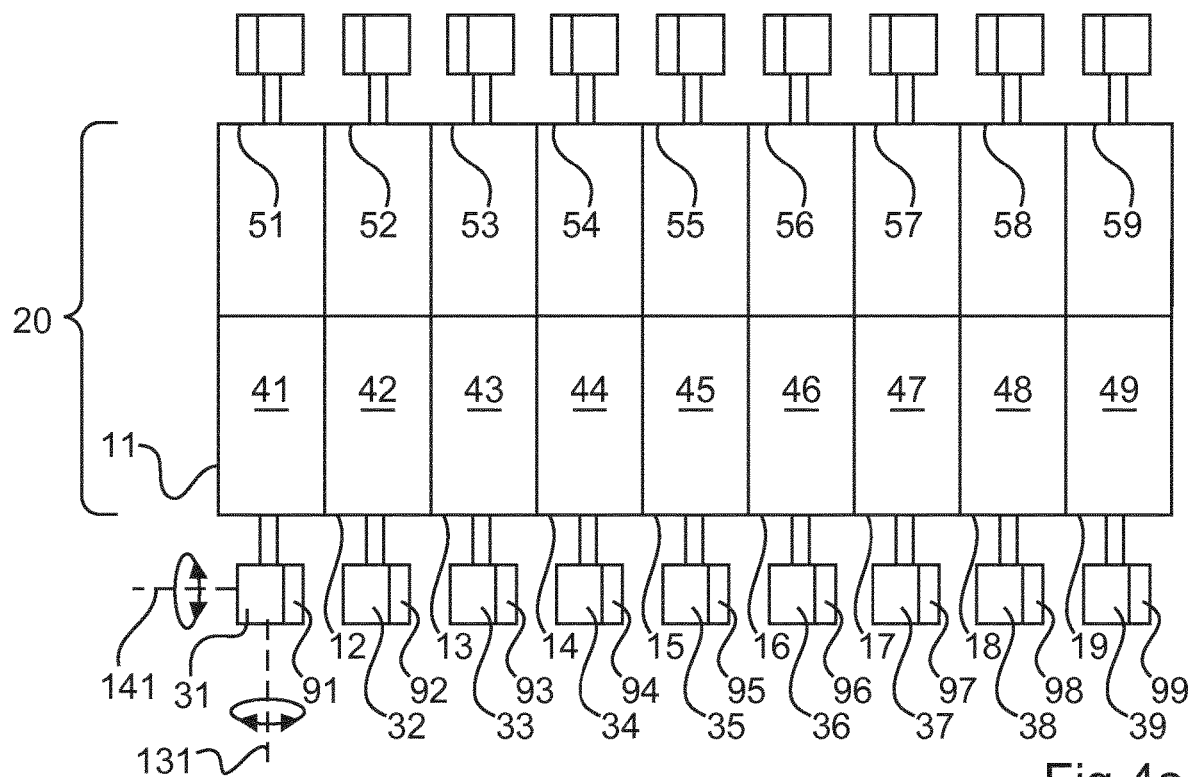
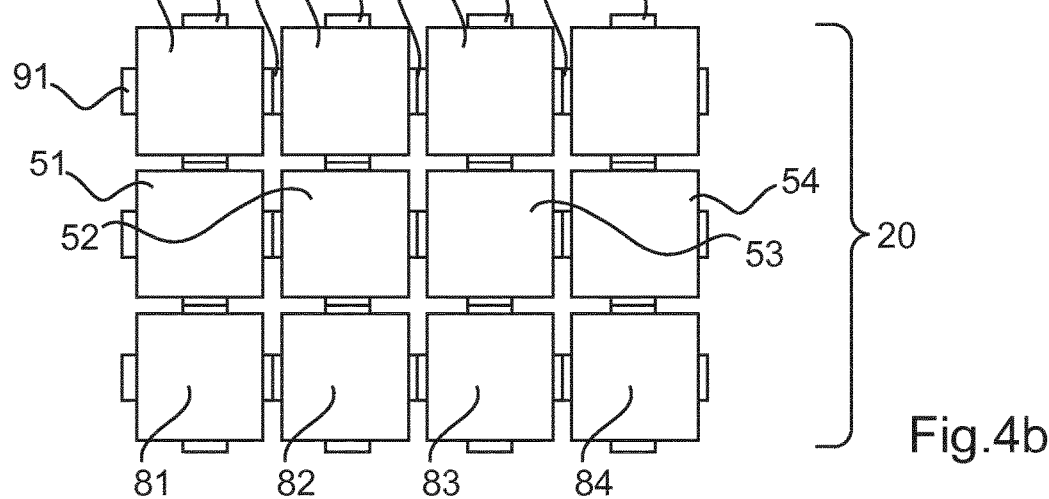
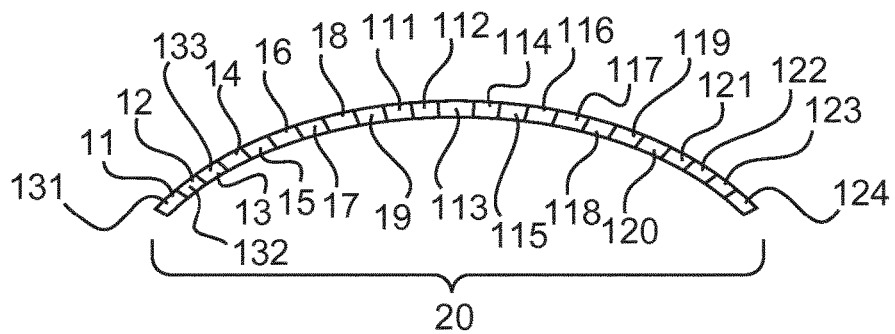
Fig.4a
Fig.4b
Fig.4c

DEVICE AND METHOD FOR ALIGNING AN X-RAY GRATING TO AN X-RAY RADIATION SOURCE, AND X-RAY IMAGE ACQUISITION SYSTEM

FIELD OF THE INVENTION

The present invention relates to a device and a method for aligning an X-ray grating to an X-ray radiation source, and an X-ray image acquisition system.

BACKGROUND OF THE INVENTION

Dark field X-ray image acquisition uses small angle scattering to obtain information that is not obtainable from normal X-ray imaging. A dark field X-ray image acquisition system uses three gratings: G0, G1, and G2. Grating G0 and G1 are small and are typically arranged close to the X-ray radiation source. The G0 grating is arranged at the X-ray radiation source and is used to provide a two-dimensional array of virtual sources. The G1 grating may modulate the amplitude or phase of the X-ray radiation. The G2 grating is used to analyze the wave front of the X-ray radiation which has travelled through an object to be imaged. The G2 grating is arranged close to the X-ray radiation detector and preferably covers the full-size of the active area of the X-ray radiation detector.

The gratings G0 and G2 consist of stripes of material that are blocking for X-ray radiation interspaced with stripes that are transparent for X-ray radiation. The X-ray blocking stripes must have a finite thickness to be able to block X-ray radiation. The grating has a focal point on the X-ray radiation source, i.e. the stripes are orientated along the optical axis of the X-ray image acquisition system. However, almost all production methods lead to an unfocused grating structure, i.e., the grating stripes are all parallel to each other.

JP 2001 206161 A describes a first absorption type grating which comprises a plurality of small gratings arrayed along the virtual cylindrical surface whose center axis is a virtual line passing through an X-ray focus and an X-ray radiation source. A phase differential image generation calculator applies a correction amount for each grating, calculating a phase deviation of the intensity change.

DE 101 36 795 A1 describes a grating which is manufactured in a flat manner and then brought into a curved shape by mechanical stress.

SUMMARY OF THE INVENTION

There may thus be a need to provide a device and a method which provide an improved alignment of X-ray gratings.

The object of the present invention is solved by the subject-matter of the independent claims; further embodiments are incorporated in the dependent claims. It should be noted that the following described aspects of the invention apply also for the X-ray image acquisition system, the method, the computer program element and the computer readable medium.

According to the present invention, a device for aligning an X-ray grating to an X-ray radiation source is provided, the device comprising: at least two flat X-ray grating segments; at least one alignment unit for aligning one of the at least two flat X-ray grating segments; wherein the at least two flat X-ray grating segments are arranged in juxtaposition and are forming an X-ray grating; wherein the at least two flat X-ray grating segments each comprise a grating surface for X-ray radiation, each grating surface comprising a geometrical center; wherein normals to each of the grating surfaces define a common plane, wherein the normals intersect the geometrical center of the grating surface; wherein at least a first of the at least two flat X-ray grating segments is rotatable around an axis that is perpendicular to the common plane; and wherein the first of the at least two flat X-ray grating segments is connected to a first of the at least one alignment unit.

At least one of the at least two flat X-ray grating segments can thus be individually aligned by the corresponding alignment unit. In doing so, the flat X-ray grating segment is connected to the alignment unit. However, in some embodiments it is possible to connect more than one flat X-ray grating segments to an alignment unit to align a plurality of flat X-ray grating segments to a focal point or normal. Due to the individual alignment of the at least one of the at least two flat X-ray grating segments of an X-ray grating, at least one section of the X-ray grating comprises grating structures which are focused to the X-ray focal spot. In a preferred exemplary embodiment, each flat X-ray segment may be aligned by an alignment unit. In that embodiment, each flat X-ray grating segment is connected to an alignment unit, i.e. each flat X-ray grating segment is connected to its own individual alignment unit in a one to one manner.

The alignment of the flat X-ray grating segments is performed such that a normal on the grating surface, i.e. a normal that is perpendicular to the grating surface, is aligned to intersect a focal point, in which the X-ray radiation source may be arranged in. Different flat X-ray grating segments comprise normals that are perpendicular to their grating surfaces which all lie in a single flat plane. An X-ray grating segment may comprise a plurality of parallel normals that are arranged in the common plane. In an example, it is preferred that the normals intersect the respective geometrical center of the flat X-ray grating segments. Furthermore, the axis around which the flat X-ray grating segments may be rotated is perpendicular to said common plane. Thus, a rotation of the flat X-ray grating segments around that axis will pivot the normals along the common plane. The normals of the flat X-ray grating segments therefore will not leave the common plane due to a rotation around the axes. Thus, a rotation of the flat X-ray grating segments will result in intersecting normals inside the plane. Furthermore, the normals of all flat X-ray grating segments can be aligned such that they intersect in a single intersection point. Consequently, the flat X-ray grating segments may be aligned to a predefined focal point to provide the optimal alignment of each section of an X-ray grating.

The invention therefore provides a segmented X-ray grating with means to orient the individual flat X-ray grating segments towards a common focal point. Those means may for example be dynamic such that a live, permanent or repeated aligning may be performed. The segments can be individually rotated around an axis by the alignment units such that the normal of each flat X-ray grating segment, i.e. the normal that is perpendicular to the grating surface, points towards a common intersection point or line on which the X-ray radiation source is located. This intersection point or line may be a focus point or line of an X-ray image acquisition system. Thus, flat X-ray grating segments with straight grating structures can be used which are easy to manufacture. Furthermore, the X-ray grating can be used for a multitude of different focal distances by accurately changing the orientation of the flat X-ray grating segments towards the current focal distance.

Furthermore, tolerances during the manufacturing of the X-ray image acquisition system and a change of an alignment of the components of an X-ray image acquisition system can be compensated by realigning the flat X-ray grating segments of the X-ray grating.

According to an example, wherein the first of the at least one alignment unit is configured to rotate the first of the at least two flat X-ray grating segments around the axis to change the angle between the normals within the common plane such that said normals intersect at a point of intersection, and to change a position of the intersection points to a single common intersection point defining a focal point of the X-ray grating.

In an example, a flat X-ray grating segment has an unfocussed grating structure.

In a further example, the flat X-ray grating segments may be orientable towards an X-ray radiation source, wherein orientable means that the flat X-ray grating segments may be aligned such that the normals intersect the X-ray source. This means that the normal that connects the focal spot and the center of the grating segment is perpendicular to the grating surface.

In an example, the focal point is arranged on a focal normal of an X-ray image acquisition system.

In another example, the distance of the focal point to the X-ray grating is variable.

According to an example, each flat X-ray grating segment is rotatable around an axis, and each is connectable to an individual of the at least one alignment units. Concerning the respective axis, the flat X-ray grating segment is then connectable to an alignment unit in a one to one manner, i.e. a single flat X-ray grating segment may be connected to a single alignment unit to be rotatable around that axis.

This means that each flat X-ray grating segment is rotatable around an individual axis. This provides an improved adjustability of the flat X-ray grating segments.

According to an example, at least one of the at least two flat X-ray grating segments is rotatable around at least two axes and/or is translatable along the at least two axes.

Thus, the X-ray grating segments can be aligned in two dimensions. This further improves the adjustability of the flat X-ray grating segments.

According to an example, the device comprises a number of flat grating segments in the range of two to hundred, preferably in the range of five to fifty, more preferably in the range of eight to twenty, most preferably ten, flat X-ray grating segments, wherein each is connectable to an individual alignment unit.

According to an example, the X-ray grating is a G2 grating of an X-ray image acquisition device.

In another example, the X-ray grating may be a grating of a computed tomography detector.

According to an example, the axes of the flat X-ray grating segments are arranged along a curve.

The arrangement of the axes of the flat X-ray grating segments along the curve may provide an X-ray grating which is pre-aligned to a certain focal point distance. The alignment of the flat X-ray grating segments may provide a fine alignment of the focal point distance. Furthermore, due to the curvature, the sections that are arranged on the beginning and the end of the curvature may have substantially the same distance to the focal point as the flat X-ray grating segments in the center of the X-ray grating.

According to an example, the grating surface of the flat X-ray grating segment has a width and a length in the range of 1 cm to 100 cm, preferably 2 cm to 80 cm, more preferably of 3 cm to 60 cm, most preferably a width of 4 cm and a height of 43 cm.

The size of the flat X-ray grating segments and their grating surfaces may be adapted to the size of the X-ray radiation detector openings. Thus, if several X-ray radiation detectors are used, each detector may be connected to a flat X-ray grating segment which is aligned to the specific position of the X-ray radiation detector with respect to the X-ray radiation source, i.e. the focal point.

According to an example, the device comprises further flat X-ray grating segments that are arranged in juxtaposition and which are arranged next to the at least two flat X-ray grating segments to form a two-dimensional matrix of flat X-ray grating segments.

This allows to arrange the flat X-ray grating segments in a matrix. Thus, the alignment of the sections of the X-ray grating can be performed with a high spatial resolution in two dimensions.

According to the present invention, also an X-ray image acquisition system is provided, the X-ray image acquisition system comprising: an X-ray radiation source; an X-ray grating assembly comprising a device according to one of the preceding claims; an X-ray radiation detector; and at least one alignment unit; wherein the X-ray grating assembly is arranged between the X-ray radiation source and the X-ray radiation detector; wherein the focal point is arranged on the X-ray radiation source; and wherein one of the at least two flat X-ray grating segments is connected to a single of the at least one alignment unit.

In an example, the X-ray grating formed by the flat X-ray segments is arranged close to the X-ray radiation detector.

The X-ray grating may thus be a G2 grating in front of the X-ray radiation detector. Since the G2 grating has the biggest size of the gratings of the X-ray grating assembly, particularly the edge sections of the X-ray grating must be aligned to the focal point position.

According to an example, the X-ray image acquisition system further comprises a processing unit, wherein the processing unit is configured to control the at least one alignment unit to change the position of the focal point.

Thus, an automatic serial or even live alignment of the flat X-ray grating segments may be performed.

According to an example, each alignment unit is individually and/or dynamically controllable by the processing unit to dynamically adjust the position of the focal point.

According to the present invention, also a method for aligning an X-ray grating to a X-ray radiation source with a device according to the description above or a system according to the description above is provided, the method comprising the following steps: a) determining a position of an X-ray radiation source with a processing unit; b) rotating a flat X-ray grating segment with an alignment unit such that a normal that is perpendicular to a grating surface of the flat X-ray grating segment intersects the X-ray radiation source, wherein the normals intersect the geometrical center of the grating surface; and c) repeating step b) for each flat X-ray grating segment.

In an example, step b) may also be performed at the same time for each X-ray grating segment of an X-ray grating.

According to the present invention, also a computer program element for controlling an apparatus according to the description above or system according to the description above is provided, which, when being executed by a processing unit, is adapted to perform the method steps according to the description above.

According to the present invention, also a computer readable medium is provided having stored the program element according to the description above.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIGS. 4a, 4b and 4c show schematic drawings of flat X-ray grating segment arrangements.

DETAILED DESCRIPTION OF EMBODIMENTS

FIG. 1 shows the device 10 for aligning an X-ray grating 20 to an X-ray radiation source 69. In this embodiment, the X-ray grating 20 is a G2 grating.

The device 10 comprises at least two flat X-ray grating segments 11-19 which are connected to alignment units 31-39, wherein one flat X-ray grating segment 11-19 is connected to one alignment unit 31-39. Thus, each flat X-ray grating segment 11-19 is connected to an own, individual alignment unit 31-39.

Figure 2:
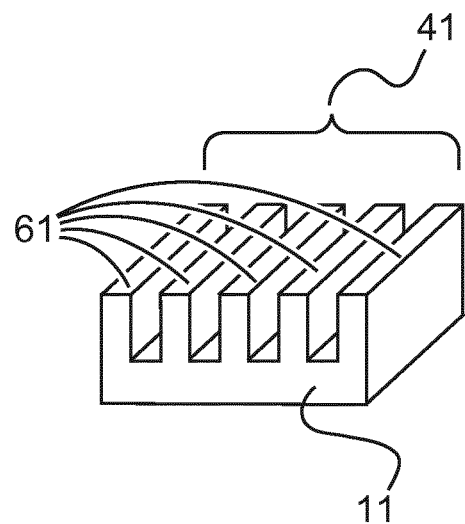
FIG. 2 shows a schematic drawing of a grating surface.

The at least two flat X-ray grating segments 11-19 are arranged in juxtaposition. They each comprise a grating surface 41-49. The grating surface 41-49 comprises grating structures 61 shown in FIG. 2 which may be configured to absorb X-ray radiation. Between the grating structures 61 are structures which are transparent for X-ray radiation.

Normals 21-29 that are perpendicular to the grating surfaces 41-49 and that intersect in the geometrical center of the flat X-ray grating segments 11-19 indicate the direction in which the grating structures 61 are oriented. The normals 21-29 of different flat X-ray grating segments 11-19 define a common plane 73. Since the normals 21-29 are perpendicular to the grating surfaces 41-49, the common plane 73 is perpendicular to the grating surfaces 41-49, too.

The alignment units 31-39 are configured to rotate the flat X-ray grating segments 11-19 around axes 131-139. The axes 131-139 are perpendicular to the plane 73, i.e. are parallel to the grating surface 41-49. A rotation around the axes 131-139 therefore results in a rotation of the normals 21-29 in the plane 73. Furthermore, the rotation results in a rotation of the grating surfaces 41-49 around the axes 131-139. Thus, the alignment units 31-39 may align the grating surfaces 41-49 of the flat X-ray grating segments 11-19.

Figure 1A:
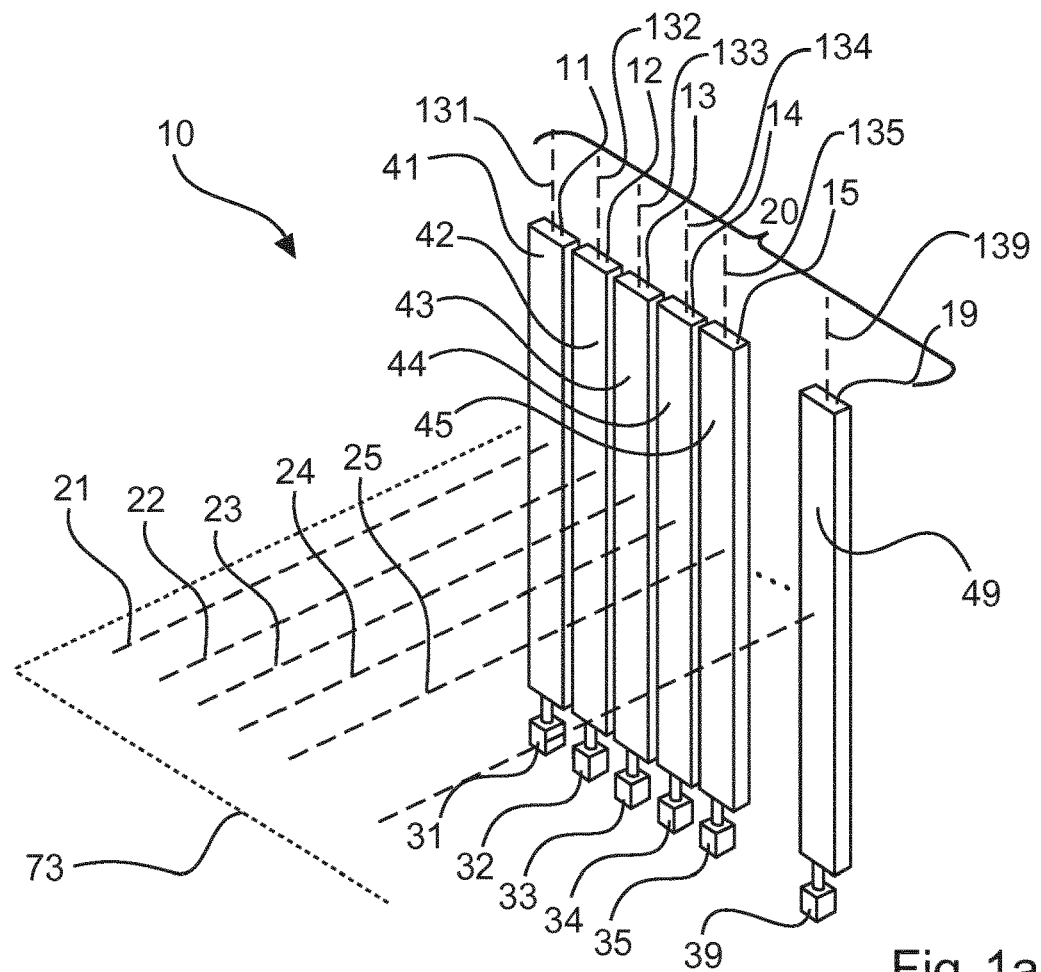
FIGS. 1a, b show schematic drawings of the device.

The number of flat X-ray grating segments 11-19 in FIG. 1a may range from two to hundred. In a dark field X-ray image acquisition system 60, the X-ray grating 20 may comprise ten to eleven flat X-ray grating segments 11-19 having a width of about 4 cm and may be arranged between an object 64 and an X-ray radiation detector 65 having a width and height of about 43 cm. Consequently, the height of the flat X-ray grating segments 11-19 may be about 43 cm.

In another embodiment, the height of the flat X-ray grating 20 may also be segmented. Thus, the height of the flat X-ray grating segments 11-19 may e.g. about 4 cm, i.e. the flat X-ray grating segments 11-19 may comprise an area of about 4 cm times 4 cm. Furthermore, that embodiment allows an alignment in height and width. An example of this embodiment may look like the embodiment of FIG. 4a or 4b discussed below.

However, the width and height of the grating surface 41-49 of the flat X-ray grating segments 11-19 may range from 1 cm to 100 cm preferably from 2 cm to 80 cm, or more preferably from 3 cm to 60 cm. The grating surface 41-49, i.e. the flat X-ray grating segments 11-19 may further comprise a square shape, a rectangular shape.

Figure 1B:
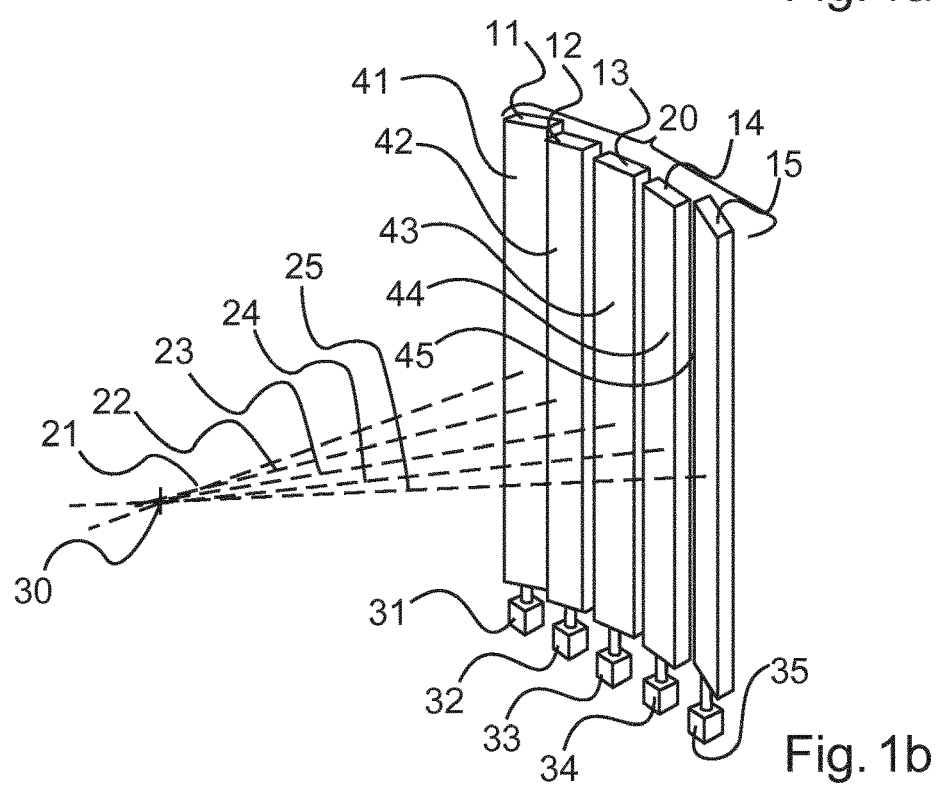

The alignment of the flat X-ray grating segments 11-19 is performed such that the normals 21-29 intersect in a single intersection point as shown in FIG. 1b. In the embodiment shown in FIG. 1b a first of the flat X-ray grating segments 11-19 that is arranged at the edge of the X-ray grating 20 is rotated most to align the respective normal 2129 to intersect the focal point 30. Moreover, a second of the flat X-ray grating segments 11-19 that is arranged closer to the center of the X-ray grating 20 is rotated less than the first flat X-ray grating segments 11-19 but more than a third of the flat X-ray grating segment 11-19 that is arranged in the center of the X-ray grating 20. The rotation of the first and second flat X-ray grating segment aligns the respective normals 21-29 to intersect the focal point 30. Each flat X-ray grating segment 11-19 may be aligned individually by the alignment units 31-39.

Figure 3:
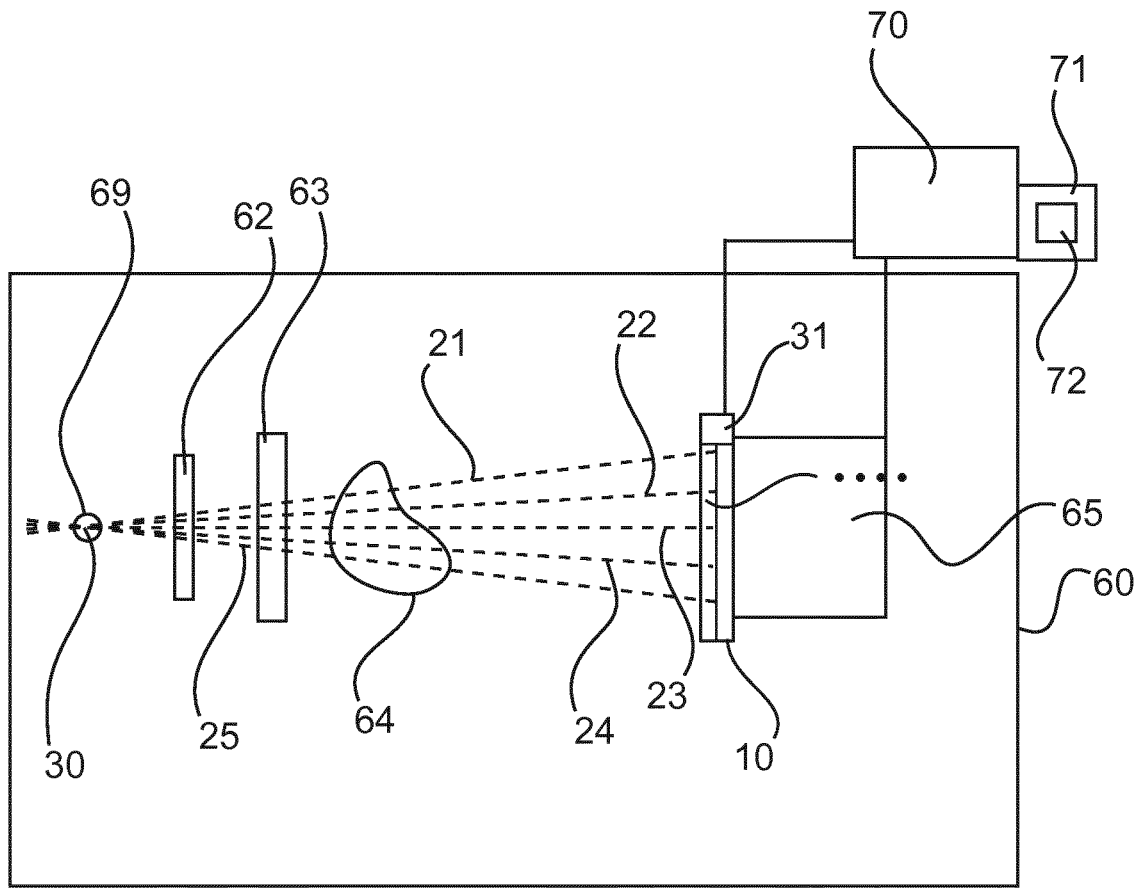
FIG. 3 shows a schematic drawing of an X-ray image acquisition system.

FIG. 3 shows an X-ray image acquisition system 60 comprising an X-ray radiation source 69, an X-ray radiation detector 65, and an X-ray grating assembly 62, 63, 10 comprising a G0 grating 62, a G1 grating 63, and the device 10.

An object 64 may be positioned between the G1 grating 63 and the G2 grating 20, wherein the object 64 may be dark field imaged.

The normals 21-29 indicating the orientation of the flat X-ray grating segments 11-19 of the device 10 intersect in the focal point 30 in which the X-ray radiation source 69 is arranged in.

A processing unit 70 may be connected to all alignment units 31-39 of the device 10, wherein in FIG. 3 for reasons of overview only a connection to the alignment unit 31 is shown. The processing unit 70 may control the alignment unit 31-39 to align the flat X-ray grating segments 11-19.

The processing unit 70 may further analyze the images acquired by the X-ray radiation detector 65 to extract alignment data for the different flat X-ray grating segments 11-19.

According to FIG. 4a, the device 10 may comprise flat X-ray grating segments 51-59 that are arranged in juxtaposition to each other, wherein each flat X-ray grating segment 51-59 is arranged in juxtaposition to one of the flat X-ray grating segments 11-19. Thus, the device 10 may comprise two rows of flat X-ray grating segments 11-19, 51-59, wherein the flat X-ray grating segments 11-19 define a first row and the flat X-ray grating segments 51-59 define a second row that is arranged next to the first row.

The flat X-ray grating segments 11-19 may further be rotatable around at least two axes 131-139, 141. In FIG. 4a only one further axis 141 is shown for overview reasons but every flat X-ray grating segment 11-19 and 51-59 may comprise two axes around which a rotation may be performed.

For rotating the flat X-ray grating segments 11-19 around the further axis 141, the device 10 may comprise further alignment units 91-99 which may rotate the flat X-ray grating segments 11-19 around the further axis. The further alignment units 91-99 may be connected to the alignment units 31-39 or directly to the flat X-ray grating segments. In an example, the further alignment unit 91-99 may be used to ensure that the normals 21-29 lie on a common plane. In another example, the further alignment may be used to amend the position of the intersection point of all normals 21-29.

FIG. 4b shows a further embodiment of the device 10. In this embodiment, the device 10 comprises a matrix of flat X-ray grating segments 11-19. In addition to the embodiment of FIG. 4a, the embodiment of FIG. 4c comprises the flat X-ray grating segments 81-84 defining a third row of flat X-ray grating segments 11-19, 51-59, 81-84. In this embodiment, the alignment units 31-39 and the alignment units 91-99 are arranged on different positions on the flat X-ray grating segments.

The embodiment of FIG. 4b may further be a computed tomography (CT) configuration. In a CT configuration, the X-ray radiation detector comprises a plurality of detector modules arranged in a matrix. One flat X-ray grating segment 11-19, 51-59, 81-84 may therefore be assigned to one detector module (not shown). Furthermore, the flat X-ray grating segments 11-19, 51-59, 81-84 may be arranged such that the gap between the flat X-ray grating segments 11-19, 51-59, 81-84 is minimized or completely avoided.

FIG. 4c shows a configuration, in which the flat X-ray grating segments 11-19 are arranged on a curvature. This means, that also the axes 131-139 are arranged on a curvature. The curvature pre-aligns the flat X-ray grating segments 11-19 such that they are pre-aligned to the center of curvature. The alignment units 31-39 may fine-tune the alignment of the flat X-ray grating segments 11-19 to precisely be aligned to the center of curvature. Furthermore, the alignment units 31-39 may amend the alignment of the flat X-ray grating segments 11-19 such that the intersection point of the normals 21-29 is on another position than the center of curvature. In one exemplary embodiment, the flat X-ray grating segments 11-19 may be arranged on a one-dimensional curvature. In another exemplary embodiment, with reference to the embodiment of FIG. 4b, the flat X-ray grating segments 11-19, 51-59, 81-84 may be aligned to a two-dimensional curvature (not shown).

Figure 5A:
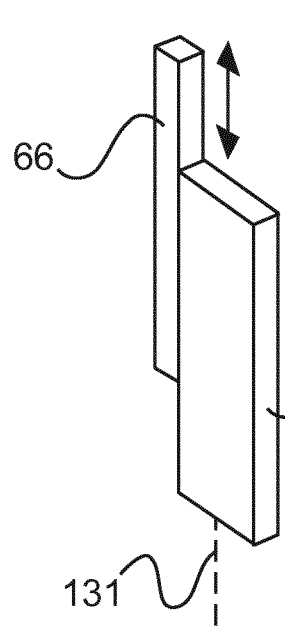
FIGS. 5a-c show schematic drawings of alignment units.
Figure 5B:
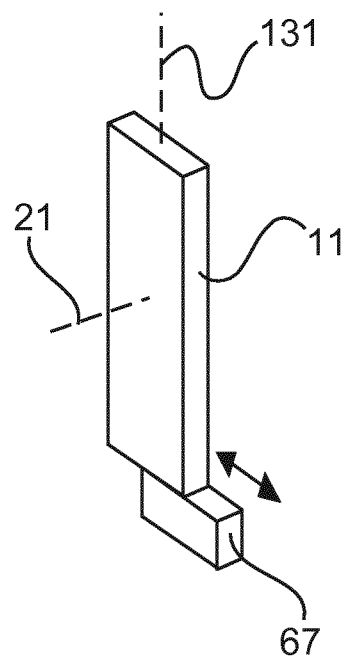
Figure 5C:
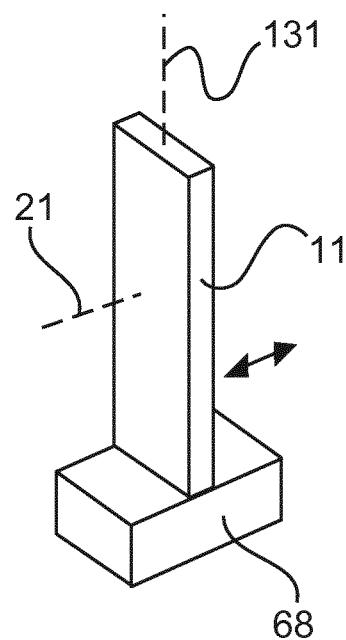

FIGS. 5a-c show embodiments of alignment units which may provide a translational alignment of the flat X-ray grating segments 11-19. In FIG. 5a and the alignment unit 66 may provide a translational alignment of the flat X-ray grating segment 11 in the direction along the axis 131.

The alignment unit 67 that is shown in FIG. 5b may provide a translational alignment in a direction that is perpendicular to the axis 131 and perpendicular to the normal 21.

The alignment unit 68 that is shown in FIG. 5c may provide a translational alignment in a direction that is parallel to normal 21.

The alignment of translational direction by the alignment units 66-68 may be provided in combination with the rotational alignment of alignment units 31-39 and 91-99. Furthermore, a third rotational alignment unit (not shown) may be provided rotating the flat X-ray grating segments 11-19 around the axis that is perpendicular to axis 131 and axis 141.

Figure 6:
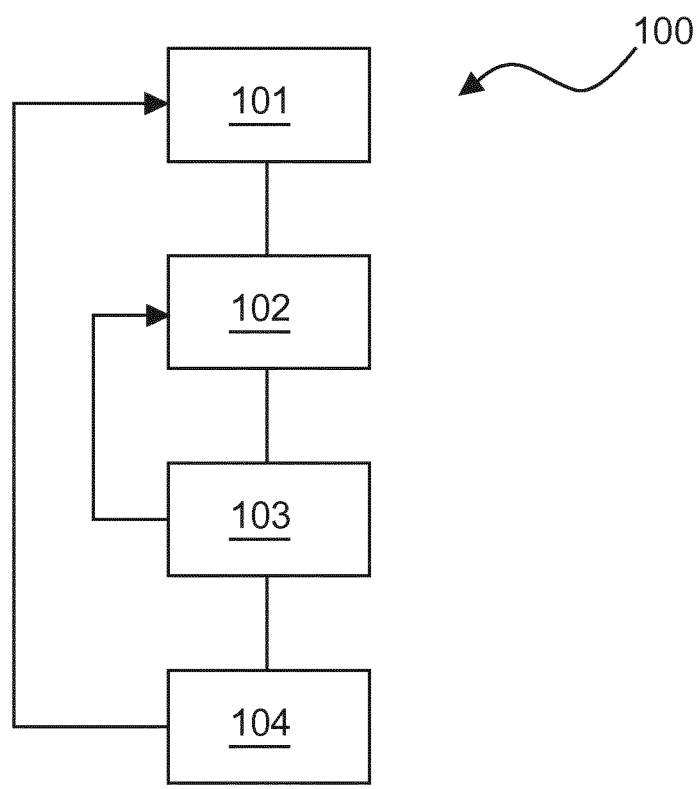
FIG. 6 shows a schematic flow chart of the method.

FIG. 6 shows a schematic flow chart of the method 100 for aligning an X-ray grating to an X-ray radiation source. The method 100 may be performed with a device 10 for aligning an X-ray grating to an X-ray radiation source or an X-ray image acquisition system 60 comprising that device 10.

FIG. 1 shows the device 10 for aligning an X-ray grating 20 to an X-ray radiation source 69. In this embodiment, the X-ray grating 20 is a G2 grating.

The device 10 comprises at least two flat X-ray grating segments 11-19 which are connected to alignment units 31-39, wherein one flat X-ray grating segment 11-19 is connected to one alignment unit 31-39. Thus, each flat X-ray grating segment 11-19 is connected to an own, individual alignment unit 31-39.

The at least two flat X-ray grating segments 11-19 are arranged in juxtaposition. They each comprise a grating surface 41-49. The grating surface 41-49 comprises grating structures 61 shown in FIG. 2 which may be configured to absorb X-ray radiation. Between the grating structures 61 are structures which are transparent for X-ray radiation.

Normals 21-29 that are perpendicular to the grating surfaces 41-49 and that intersect the geometrical center of the flat X-ray grating segments 11-19 indicate the direction in which the grating structures 61 are oriented. The normals 21-29 of different flat X-ray grating segments 11-19 define a common plane 73. Since the normals 21-29 are perpendicular to the grating surfaces 41-49, the common plane 73 is perpendicular to the grating surfaces 41-49, too.

The alignment unit 31-39 is configured to rotate the flat X-ray grating segment 11-19 around axes 131-139. The axes 131-139 are perpendicular to the plane 73, i.e. are parallel to the grating surface 41-49. A rotation around the axes 131-139 therefore results in a rotation of the normals 21-29 in the plane 73. Furthermore, the rotation results in a rotation of the grating surface 41-49 around the axes 131-139. Thus, the alignment units 31-39 may align the grating surfaces 41-49 of the flat X-ray grating segments 11-19.

The number of flat X-ray grating segments 11-19 in FIG. 1a may range from two to hundred. In a dark field X-ray image acquisition system 60, the X-ray grating 20 may comprise ten to eleven flat X-ray grating segments 11-19 having a width of about 4 cm and may be arranged between an object 64 and an X-ray radiation detector 65 having a width and height of about 43 cm. Consequently, the height of the flat X-ray grating segments 11-19 may be about 43 cm.

In another embodiment, the height of the flat X-ray grating 20 may also be segmented. Thus, the height of the flat X-ray grating segments 11-19 may e.g. about 4 cm, i.e. the flat X-ray grating segments 11-19 may comprise an area of about 4 cm times 4 cm. Furthermore, that embodiment allows an alignment in height and width. An example of this embodiment may look like the embodiment of FIG. 4a or 4b discussed below.

However, the width and height of the grating surface 41-49 of the flat X-ray grating segments 11-19 may range from 1 cm to 100 cm preferably from 2 cm to 80 cm, or more preferably from 3 cm to 60 cm. The grating surface 41-49, i.e. the flat X-ray grating segments 11-19 may further comprise a square shape, a rectangular shape.

The alignment of the flat X-ray grating segments 11-19 is performed such that the normals 21-29 intersect in a single intersection point as shown in FIG. 1b. In the embodiment shown in FIG. 1b a first of the flat X-ray grating segments 11-19 that is arranged at the edge of the X-ray grating 20 is rotated most to align the respective normal 2129 to intersect the focal point 30. Moreover, a second of the flat X-ray grating segments 11-19 that is arranged closer to the center of the X-ray grating 20 is rotated less than the first flat X-ray grating segments 11-19 but more than a third of the flat X-ray grating segment 11-19 that is arranged in the center of the X-ray grating 20. The rotation of the first and second flat X-ray grating segment aligns the respective normals 21-29 to intersect the focal point 30. Each flat X-ray grating segment 11-19 may be aligned individually by the alignment units 31-39.

FIG. 3 shows an X-ray image acquisition system 60 comprising an X-ray radiation source 69, an X-ray radiation detector 65, and an X-ray grating assembly 62, 63, 10 comprising a G0 grating 62, a G1 grating 63, and the device 10.

An object 64 may be positioned between the G1 grating 63 and the G2 grating 20, wherein the object 64 may be dark field imaged.

The normals 21-29 indicating the orientation of the flat X-ray grating segments 11-19 of the device 10 intersect in the focal point 30 in which the X-ray radiation source 69 is arranged in.

A processing unit 70 may be connected to all alignment units 31-39 of the device 10, wherein in FIG. 3 for reasons of overview only a connection to the alignment unit 31 is shown. The processing unit 70 may control the alignment unit 31-39 to align the flat X-ray grating segments 11-19.

The processing unit 70 may further analyze the images acquired by the X-ray radiation detector 65 to extract alignment data for the different flat X-ray grating segments 11-19.

In the first step a), a position of an X-ray radiation source may be determined 101 with a processing unit. This may for example be performed by maximizing the transmission and the visibility of the interferometer at the edges of the X-ray radiation detector by using the flat X-ray grating segments 11 and 15 that is arranged at the edge of the X-ray grating 20.

In a second step b), the flat X-ray grating segments may be rotated 102 with an alignment unit such that a normal that is perpendicular to a grating surface of the flat X-ray grating segment intersects the X-ray radiation source.

According to FIG. 4a, the device 10 may comprise flat X-ray grating segment 51-59 that is arranged in juxtaposition to each other, wherein each flat X-ray grating segment 51-59 is arranged in juxtaposition to one of the flat X-ray grating segments 11-19. Thus, the device 10 may comprise two rows of flat X-ray grating segments 11-19, 51-59, wherein the flat X-ray grating segments 11-19 define a first row and the flat X-ray grating segments 51-59 define a second row that is arranged next to the first row.

The flat X-ray grating segments 11-19 may further be rotatable around at least two axes 131-139, 141. In FIG. 4a only one further axis 141 is shown for overview reasons but every flat X-ray grating segment 11-19 and 51-59 may comprise two axes around which a rotation may be performed.

For rotating the flat X-ray grating segments 11-19 around the further axis 141, the device 10 may comprise further alignment units 91-99 which may rotate the flat X-ray grating segments 11-19 around the further axis. The further alignment units 91-99 may be connected to the alignment units 31-39 or directly to the flat X-ray grating segments. In an example, the further alignment unit 91-99 may be used to ensure that the normals 21-29 lie on a common plane. In another example, the further alignment may be used to amend the position of the intersection point of all normals 21-29.

FIG. 4b shows a further embodiment of the device 10. In this embodiment, the device 10 comprises a matrix of flat X-ray grating segments 11-19. In addition to the embodiment of FIG. 4a, the embodiment of FIG. 4c comprises the flat X-ray grating segments 81-84 defining a third row of flat X-ray grating segments 11-19, 51-59, 81-84. In this embodiment, the alignment units 31-39 and the alignment units 91-99 are arranged on different positions on the flat X-ray grating segments.

The embodiment of FIG. 4b may further be a computed tomography (CT) configuration. In a CT configuration, the X-ray radiation detector comprises a plurality of detector modules arranged in a matrix. One flat X-ray grating segment 11-19, 51-59, 81-84 may therefore be assigned to one detector module (not shown). Furthermore, the flat X-ray grating segments 11-19, 51-59, 81-84 may e.g. arranged such that the gap between the flat X-ray grating segments 11-19, 51-59, 81-84 is minimized or completely avoided.

FIG. 4c shows a configuration, in which the flat X-ray grating segments 11-19 are arranged on a curvature. This means, that also the axes 131-139 are arranged on a curvature. The curvature pre-aligns the flat X-ray grating segments 11-19 such that they are pre-aligned to the center of curvature. The alignment units 31-39 may fine-tune the alignment of the flat X-ray grating segments 11-19 to precisely be aligned to the center of curvature. Furthermore, the alignment units 31-39 may amend the alignment of the flat X-ray grating segments 11-19 such that the intersection point of the normals 21-29 is on another position than the center of curvature. In one exemplary embodiment, may be aligned to a one-dimensional curvature. In another exemplary embodiment, with reference to the embodiment of FIG. 4b, the flat X-ray grating segments 11-19, 51-59, 81-84 may be aligned to a two-dimensional curvature (not shown).

FIGS. 5a-c show embodiments of alignment units which may provide a translational alignment of the flat X-ray grating segments 11-19. In FIG. 5a and the alignment unit 66 may provide a translational alignment of the flat X-ray grating segment 11 in the direction along the axis 131.

The alignment unit 67 that is shown in FIG. 5b may provide a translational alignment in a direction that is perpendicular to the axis 131 and perpendicular to the normal 21.

The alignment unit 68 that is shown in FIG. 5c may provide a translational alignment in a direction that is parallel to normal 21.

The alignment of translational direction by the alignment units 66-68 may be provided in combination with the rotational alignment of alignment units 31-39 and 91-99. Furthermore, a third rotational alignment unit (not shown) may be provided rotating the flat X-ray grating segments 11-19 around the axis that is perpendicular to axis 131 and axis 141.

In a further step c), step b) may be repeated 103 for each flat X-ray grating segment of the X-ray grating. This means, and the alignment of the flat X-ray grating segments may be performed as a series of alignments of the flat X-ray grating segments.

In another example, the alignment of the flat X-ray grating segments may be performed at the same time for all flat X-ray grating segments of the X-ray grating.

In an even further step d), the steps a) to c) may be repeated 104 after a predetermined period. This means, that the alignment of the flat X-ray grating segments may be performed several times e.g. to avoid a misalignment due to temperature variations or vibrations.

In another exemplary embodiment of the present invention, a computer program or a computer program element is provided that is characterized by that is adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for aligning an X-ray grating to an X-ray radiation source, the device comprising:
    at least two flat X-ray grating segments;
    at least one alignment unit for aligning one of the at least two flat X-ray grating segments;
    wherein the at least two flat X-ray grating segments are arranged in juxtaposition and are forming an X-ray grating;
    wherein the at least two flat X-ray grating segments each comprise a grating surface for X-ray radiation, each grating surface comprising a geometrical center;
    wherein normals to each of the grating surfaces define a common plane, wherein the normals intersect the geometrical center of the grating surface;
    wherein at least a first of the at least two flat X-ray grating segments is rotatable around an axis that is perpendicular to the common plane; and
    wherein the first of the at least two flat X-ray grating segments is connected to a first of the at least one alignment unit.

2. The device according to claim 1, wherein the first of the at least one alignment unit is configured to rotate the first of the at least two flat X-ray grating segments around the axis to change the angle between the normals within the common plane such that said normals intersect at a point of intersection, and to change a position of the intersection points to a single common intersection point defining a focal point of the X-ray grating.

3. The device according to claim 1, wherein each flat X-ray grating segment is rotatable around an axis, and each is connectable to individual of at least one alignment units.

4. The device according to claim 1, wherein at least one of the at least two flat X-ray grating segments is rotatable around at least two axes and/or is translatable along the at least two axes.

5. The device according to claim 1, wherein the device comprises a number of flat X-ray grating segments in the range of two to hundred, wherein each is connectable to an individual of the at least one alignment unit.

6. The device according to claim 1, wherein the X-ray grating is a G2 grating of an X-ray image acquisition device.

7. The device according to claim 1, wherein the axes of the flat X-ray grating segments are arranged along a curve.

8. The device according to claim 1, wherein the grating surface has a width and a length in the range of 1 cm to 100 cm, and a height of 43 cm.

9. The device according to claim 1, wherein the device comprises further flat X-ray grating segments that are arranged in juxtaposition and which are arranged next to the at least two flat X-ray grating segments to form a two-dimensional matrix of flat X-ray grating segments.

10. An X-ray image acquisition system comprising:
    an X-ray radiation source;
    an X-ray grating assembly comprising a device comprising:
        at least two flat X-ray grating segments;
        at least one alignment unit for aligning one of the at least two flat X-ray grating segments;
        wherein the at least two flat X-ray grating segments are arranged in juxtaposition and are forming an X-ray grating;

wherein the at least two flat X-ray grating segments each comprise a grating surface for X-ray radiation, each grating surface comprising a geometrical center;

wherein normals to each of the grating surfaces define a common plane, wherein the normals intersect the geometrical center of the grating surface;

wherein at least a first of the at least two flat X-ray grating segments is rotatable around an axis that is perpendicular to the common plane; and wherein the first of the at least two flat X-ray grating segments is connected to a first of the at least one alignment unit;

an X-ray radiation detector;

wherein the X-ray grating assembly is arranged between the X-ray radiation source and the X-ray radiation detector.

11. The X-ray image acquisition system according to claim 10, wherein the X-ray image acquisition system further comprises a processor configured to control the at least one alignment unit to change the position of a focal point.

12. The X-ray image acquisition system according to claim 10, wherein each alignment unit is individually and/or dynamically controllable by the processor to dynamically adjust the position of a focal point.

13. A method for aligning an X-ray grating to a X-ray radiation source, the method comprising:

providing at least two flat X-ray grating segments;

aligning one of the at least two flat X-ray grating segments with at least one alignment unit;

wherein the at least two flat X-ray grating segments are arranged in juxtaposition and are forming an X-ray grating;

wherein the at least two flat X-ray grating segments each comprise a grating surface for X-ray radiation, each grating surface comprising a geometrical center;

wherein normals to each of the grating surfaces define a common plane, wherein the normals intersect the geometrical center of the grating surface;

wherein at least a first of the at least two flat X-ray grating segments is rotatable around an axis that is perpendicular to the common plane; and wherein the first of the at least two flat X-ray grating segments is connected to a first of the at least one alignment unit.

14. A non-transitory computer-readable medium having one or more executable instructions stored thereon which, when executed by at least one processor, cause the at least one processor to perform a method for aligning an X-ray grating to a X-ray radiation source, the method comprising:

providing at least two flat X-ray grating segments;

aligning one of the at least two flat X-ray grating segments with at least one alignment unit;

wherein the at least two flat X-ray grating segments are arranged in juxtaposition and are forming an X-ray grating;

wherein the at least two flat X-ray grating segments each comprise a grating surface for X-ray radiation, each grating surface comprising a geometrical center;

wherein normals to each of the grating surfaces define a common plane, wherein the normals intersect the geometrical center of the grating surface;

wherein at least a first of the at least two flat X-ray grating segments is rotatable around an axis that is perpendicular to the common plane; and wherein the first of the at least two flat X-ray grating segments is connected to a first of the at least one alignment unit.

* * * * *